(12) United States Patent
Looney

(10) Patent No.: US 10,514,371 B2
(45) Date of Patent: Dec. 24, 2019

(54) REACTIVE DIFFUSIVE GRADIENT IN THIN-FILM SAMPLER AND MERCURY SPECIATION BY USE OF SAME

(71) Applicant: Savannah River Nuclear Solutions, LLC, Aiken, SC (US)

(72) Inventor: Brian B. Looney, Aiken, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 110 days.

(21) Appl. No.: 15/800,534

(22) Filed: Nov. 1, 2017

(65) Prior Publication Data
US 2019/0128863 A1 May 2, 2019

(51) Int. Cl.
*G01N 33/20* (2019.01)
*G01N 1/40* (2006.01)

(52) U.S. Cl.
CPC ........... *G01N 33/20* (2013.01); *G01N 1/4044* (2013.01); *G01N 1/4077* (2013.01); *G01N 2001/4016* (2013.01); *G01N 2001/4088* (2013.01); *Y10T 436/255* (2015.01)

(58) Field of Classification Search
CPC .... G01N 33/20; G01N 1/4005; G01N 1/4044; G01N 1/4077; G01N 2001/4088; Y10T 436/25; Y10T 436/25125; Y10T 436/25375; Y10T 436/255; Y10T 436/2575
USPC ..... 436/73, 80, 81, 174, 175, 177, 178, 180; 422/420, 421, 422, 527, 534, 535
See application file for complete search history.

(56) References Cited

U.S. PATENT DOCUMENTS

| | | | |
|---|---|---|---|
| 3,693,323 | A | 9/1972 | Gant |
| 3,714,562 | A | 1/1973 | McNerney |
| 3,771,960 | A | 11/1973 | Kim et al. |
| 3,924,219 | A | 12/1975 | Braun |
| 4,423,407 | A | 12/1983 | Zuckerman |
| 5,229,321 | A | 7/1993 | Takami |
| 5,492,627 | A | 2/1996 | Hagen et al. |

(Continued)

FOREIGN PATENT DOCUMENTS

| | | |
|---|---|---|
| CN | 101629881 | 1/2010 |
| CN | 202057518 | 11/2011 |

(Continued)

OTHER PUBLICATIONS

Tafurt-Cardona et al. Analytica Chimica Acta, vol. 887, Aug. 10, 2015, pp. 38-44.*

(Continued)

*Primary Examiner* — Maureen Wallenhorst
(74) *Attorney, Agent, or Firm* — Dority & Manning, P.A.

(57) ABSTRACT

Sampling devices for mercury speciation protocols are described. Devices can be utilized to separate mercury species from one another as a sample diffuses through a sampling device. Methods can determine the presence or quantity of targeted mercury species in a fluid sample. The devices are passive sampling devices based upon diffusion gradient in thin film (DGT) passive sampling devices. Devices include a reactant component and a sequesterant component that selectively react with a targeted species and retain a species (or a reaction product of a species) of a sample flow. Remaining mercury species can optionally be captured downgradient, for instance at an ion exchange resin.

20 Claims, 4 Drawing Sheets

(56) References Cited

U.S. PATENT DOCUMENTS

| | | | |
|---|---|---|---|
| 5,558,771 | A | 9/1996 | Hagen et al. |
| 6,129,843 | A | 10/2000 | Petty et al. |
| 6,823,749 | B1 | 11/2004 | Welsh et al. |
| 7,059,206 | B1 | 6/2006 | Kingston et al. |
| 7,222,546 | B2 | 5/2007 | St. Germain |
| 7,285,419 | B2 | 10/2007 | Shade |
| 8,011,239 | B1 | 9/2011 | Chadwick et al. |
| 8,034,246 | B2 | 10/2011 | Gustafsson |
| 8,287,726 | B2 | 10/2012 | Williams et al. |
| 8,828,731 | B2 | 9/2014 | Alper |
| 9,199,192 | B2 | 12/2015 | Cooper |
| 9,399,912 | B2 | 7/2016 | McAlary et al. |
| 2003/0118492 | A1* | 6/2003 | Cooper .......... B01D 53/64 423/210 |
| 2003/0228699 | A1* | 12/2003 | Shade .......... G01N 30/88 436/81 |
| 2005/0199047 | A1 | 9/2005 | Adams et al. |
| 2006/0257286 | A1 | 11/2006 | Adams |
| 2007/0122870 | A1 | 5/2007 | Turley et al. |
| 2009/0032472 | A1 | 2/2009 | Krogue |
| 2009/0045149 | A1 | 2/2009 | Murray et al. |
| 2011/0068046 | A1 | 3/2011 | Tullos |
| 2011/0070597 | A1 | 3/2011 | Vlahos et al. |
| 2017/0023536 | A1 | 1/2017 | Finnigan |
| 2018/0017468 | A1* | 1/2018 | Point .......... G01N 1/10 |

FOREIGN PATENT DOCUMENTS

| | | |
|---|---|---|
| CN | 103743655 | 4/2014 |
| CN | 204188444 | 4/2015 |
| CN | 204188445 | 4/2015 |
| CN | 105080519 | 11/2015 |
| CN | 105148847 | 12/2015 |
| CN | 205679503 | 11/2016 |
| CN | 206074593 | 5/2017 |
| DE | 825909 C | 1/1951 |
| KR | 101682421 | 12/2016 |
| WO | WO 2008/045599 | 4/2008 |
| WO | WO 2009/017479 | 2/2009 |
| WO | WO 2010/014852 | 2/2010 |
| WO | WO 2016/128686 | 8/2016 |

OTHER PUBLICATIONS

Bireta, Paul. Application of Diffusive Gradient in Thin-Film Passive Samplers to Assess Mercury Availability and Mobility in a Fresh Water River System. 2015.

Clarisse, O., G.R. Lotufo, H. Hintelmann, E.P.H. Best. Biomonitoring and assessment of monomethylmercury exposure in aqueous systems using the DGT technique. *Science of the Total Environment* 416 (2012) 449-454.

Clarisse, O., Holger Hintelmann. Measurements of Dissolved Methymercury in Natural Waters Using Diffusion Gradients in Thin Film (DGT). Journal of Environmental Monitoring. www.rsc.org/jem. 2006. p. 1242-1247.

DGT—for Measurements in Water, Soils, and Sediments.

Docekalova, H., P. Divis. Application of Diffusion Gradient in Thin Film (DGT) to Measurement of Mercury in Aquatic Systems. Science Direct. ELSEVIER. 2004.

Fernandez-Gomez, C., B. Dimock, H. Hintelmann, S. Diez. Development of the DGT Technique for Hg Measurements in Water: Comparison of Three Different Types of Samples in Laboratory Assays, Chemosphere, ELSEVEIR. 2011.

Fernandez-Gomez, C., J.M. Bayona, S. Diez. Diffusive gradients in thin films for predicting methylmercury bioavailability in freshwaters after photodegradation. *Science Direct*. 2015.

Fernandez-Gomez, Cristal, Josep M. Bayona, Sergie Diez, Comparison of different types of diffusive gradient in thin film samplers for measurement of dissolved methylmercury in freshwater, *Science Direct* 2014.

Gao, Yue, Sam De Craemer, Willy Baeyens. A novel method for the determination of dissolved methylmercury concentrations using diffusive gradients in thin films technique. *Science Direct*. 2014.

Huttenloch, Petra, Karl Ernst Roehl, and Kurt Czurda. Use of Copper Shavings to Remove Mercury from Contaminated Groundwater or Wastewater by Amalgamation. *Environ. Sci. Technol.* 2003, 37, 4269-4273.

Manning, Gus. Non-Charcoal Diffusive Samplers. Jun. 2007.

Michaud, Jon-Pierre, James Quackenboss. A Short-Term Diffusive Sampler for Nitrogen Dioxide Monitoring in Epidemiology. Air & Waste Management Association. vol. 41, No. 11, 1483-1488. 1991.

Panichev, N.A., S.E. Panicheva. Influence of Different Cooking Procedure on the Hg Concentration in Fish. Fisheriessciences,com. 2015. p. 64.

Pauller, M.H., Brian Looney, Anna Knox, Dennis Jackson, Nancy Halverson, Wendy Kuhne, Michele Harmon. Development of methods for measuring bioavailable metals & mercury species using Diffusive Gradients in Thin film (DGT) technology. Oct. 3, 2017.

Pauller, M.H., James W. Littrell. Long Term Changes in Mercury Concentration in Fish From the Middle Savannah River. Science Direct, ELSEVIER. 2007.

Pei, Jianhong, Mary-Lou Tercier-Waeber, Jacques Buffle, Giovanni Carlo Fiaccabrino, and Milena Koudelka-Hep. Individually Addressable Gel-Integrated Voltammetric Microelectrode Array for High-Resolution Measurement of Concentration Profiles at Interfaces. *Anal. Chem.*, 2001, 73, 2273-2281.

Peinjenburg, Willie JGM, Peter R. Teasdale, Dannie, Reible, Julie Mondon, William W. Bennett, and Peter GC Campbell. Passive Sampling Methods for Contaminated Sediments: State of the Science for Metals. *Int. Env. Assessment & Management*, vol. 10, No. 2—pp. 179-196, 2014.

Pelcova, Pavlina, Hana Docekalova, Andrea Kleckerova, Development of the Diffusive Gradient in Thin Film Technique for the Measurement of Labile Mercury Species in Waters. Analytica Chimica Acta. ELSEVIER. 2013.

Skogvold, Silje Marie. Development and properties of nontoxic solid electrodes for environmental surveillance. Feb. 2009.

Methods and recent advances in speciation analysis of mercury chemical species in environmental samples, Chemical Speciation and Bioavailability—Mar. 2016, 17 pgs., Amde, M. et al.

A Review on Recent Applications of High-Performance Liquid Chromatography in Metal Determination and Speciation Analysis, Crit Rev Anal Chem. Nov. 2017. 2 pgs. Rekhi, H et al.

Recent Advances in the Analysis of Mercury in Water—Review, Feb. 2016, Kallithrakas, N. et al.

* cited by examiner

REACTIVE DIFFUSIVE GRADIENT IN THIN-FILM SAMPLER AND MERCURY SPECIATION BY USE OF SAME

FEDERAL RESEARCH STATEMENT

This invention was made with government support under Contract No. DE-AC09-08SR22470 awarded by the U.S. Department of Energy. The government has certain rights in the invention.

BACKGROUND

Mercury (Hg) is an important and persistent environmental pollutant that is bioaccumulative and toxic in even small amounts. There are many stable Hg species, with different species exhibiting different characteristics including toxicity, solubility, mobility and bioavailability. Organic Hg and in particular methylmercury ($[CH_3Hg]^+$; MeHg) is one of the most toxic Hg species affecting human and animal health. Hg can be found naturally in the environment as well as a result of anthropogenic activities such as mining, Hg manufacture and disposal, and fossil fuel combustion.

Hg contamination has become a global concern as it is often released into the atmosphere in one location with impact on ecosystems in another location, which can be thousands of kilometers away. When Hg enters in an aqueous system, it is subject to methylation, forming MeHg, and demethylation, forming inorganic Hg (InHg), primarily ionic $Hg^{2+}$ and labile complexes such as $HgCl_2^0$. Once in the biosystem, MeHg partitions into periphyton, plankton and biota that are eaten by invertebrates and fish. As a result, MeHg bio-magnifies as it accumulates throughout and up the food chain.

Due to both the toxicity as well as the bio-magnification in the food chain, monitoring both total Hg and Hg species is of high importance to assess potential impacts on human and animal health as well as the environment; additionally, understanding spatial and seasonal variability and lability of Hg species in the environment is important to refine the technically based assessment of risks.

What are needed in the art are methods and devices that can provide simple and affordable protocols for Hg monitoring and risk assessment. More specifically, what is needed is a device that can effectively provide information with regard to the presence and/or quantity of particular Hg species in an environment so as to better assess risk. Moreover, methods and devices that differentiate organic Hg from inorganic and elemental Hg and which can function as surrogates for aquatic organisms by simply and accurately determining the presence and/or concentration of specific Hg species that are bioavailable to aquatic organisms could be of great benefit.

SUMMARY

According to one embodiment, disclosed is a passive Hg sampling device. A device can include an upgradient end (i.e., that end of the device placed in contact with a sample) and a downgradient end (i.e., that end of the device toward which the sample components diffuse). The device also includes a diffusive zone and a capture zone that is downgradient of the diffusive zone. In addition, a device includes a reactant that is configured to react with a first Hg species and a sequesterant that is configured to selectively retain a second Hg species. The reactant and the sequesterant are each independently located in either the diffusive zone or the capture zone. In one embodiment, a device can also include in the capture zone an agent that is configured to retain a third Hg species, for instance in those embodiments in which the reactant and the sequesterant are both located in the diffusive zone.

Also disclosed is a method for selectively sampling a Hg species. A method can include contacting a fluid sample that includes a first Hg species with the upgradient end of a passive sampling device. Upon this contact, the first Hg species can react with the reactant to form the second Hg species, and the second Hg species (i.e., the reaction product) can then be selectively retained by the sequesterant. A method can also include analyzing the capture layer and thereby determining the presence or quantity of the first Hg species in the fluid sample. For instance through analysis of the capture layer, the presence or quantity of the second Hg species can be directly or indirectly determined, and this data can provide information concerning the first Hg species. In those embodiments in which the capture layer includes an agent that is configured to retain a third Hg species, the analysis of the capture layer can be combined with information regarding the total mercury content of the sample source, and information about the first Hg species can be obtained through comparison of the results of the two analyses.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
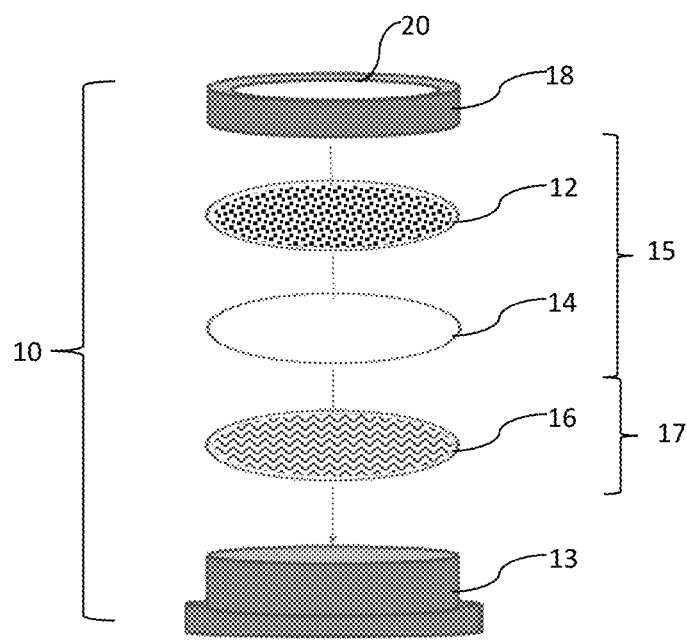
FIG. 1 presents a schematic representation of a diffusive gradient in thin-films (DGT) passive sampling device as is known in the art.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to passive sampling devices that can be beneficially utilized in Hg speciation protocols. More specifically, disclosed devices can be utilized to separate Hg species from one another as a sample diffuses from the upgradient end to the downgradient end of a sampling device, so as to accurately determine the presence or quantity of different Hg species in a fluid sample. As utilized herein, the term "fluid sample" generally refers to any sample that is composed primarily (but not exclusively) of gaseous and/or liquid fluid(s) and includes a gaseous sample such as air, a vaporous sample such as steam, or a liquid sample such as an aqueous sample as may be obtained from any source (e.g., stream water, lake water, pore water, etc.). Beneficially, the devices are passive sampling devices, and as such no activity or energy addition is necessary during functional use of the device. Accordingly, a device need only be located in contact with a sample, and the device can passively function to retain one or more Hg species of the sample within one or more zones of the device.

The passive sampling devices are based upon DGT sampling devices. In contrast to previously known DGT sampling devices, however, the disclosed devices include one or more additional functional materials as reactant and sequesterant that can function within the device to separate Hg species of a fluid sample from one another.

As illustrated in FIG. 1 in an exploded view, a DGT sampling device 10 as generally known is a passive sampler that can accumulate solutes through zones encased by use of a removable cap 18 and a base 13. The primary zones of a device generally include a diffusive zone 15 and a capture zone 17. Each zone 15, 17 can include one or more separate layers. For instance, in the illustrated embodiment, the diffusive zone 15 includes two separate layers including a filter layer 12, and a diffusion layer 14 (generally in the form of a hydrogel). In the illustrated embodiment, the capture zone 17 includes a single capture layer 16 (also generally in the form of a hydrogel), but this zone can optionally include additional layers (e.g., additional capture layers designed to capture different analytes). When previously known devices as illustrated in FIG. 1 are deployed in a solution Hg species including both organic and inorganic species can diffuse through the first two layers 12, 14 of the diffusive zone 15 and be retained in the capture layer 16 of the capture zone 17. Generally, Hg retention in the capture zone 17 is provided by incorporation of an ion-exchange resin in a capture layer 16. The filter layer 12 of the diffusive zone 15 is generally present, particularly for environmental applications, but not necessarily present (for instance in laboratory techniques).

The composition of the components of the diffusive zone 15 (e.g., a diffusion layer 14 and a filter layer 12) can vary, depending upon the particular sample sources and analytes being targeted. For instance, Hg has a high binding capacity with amide groups. As such, for measurement of Hg in aquatic systems, polyacrylamide gels that are often used in other types of DGT samplers are generally not used in the diffusive zone of a DGT designed for Hg capture. In general, both the diffusion layer 14 and the capture layer 16 are based on hydrogels, with the hydrogel of the capture layer 16 including a suitable capture agent for the analyte of interest.

Figure 2:
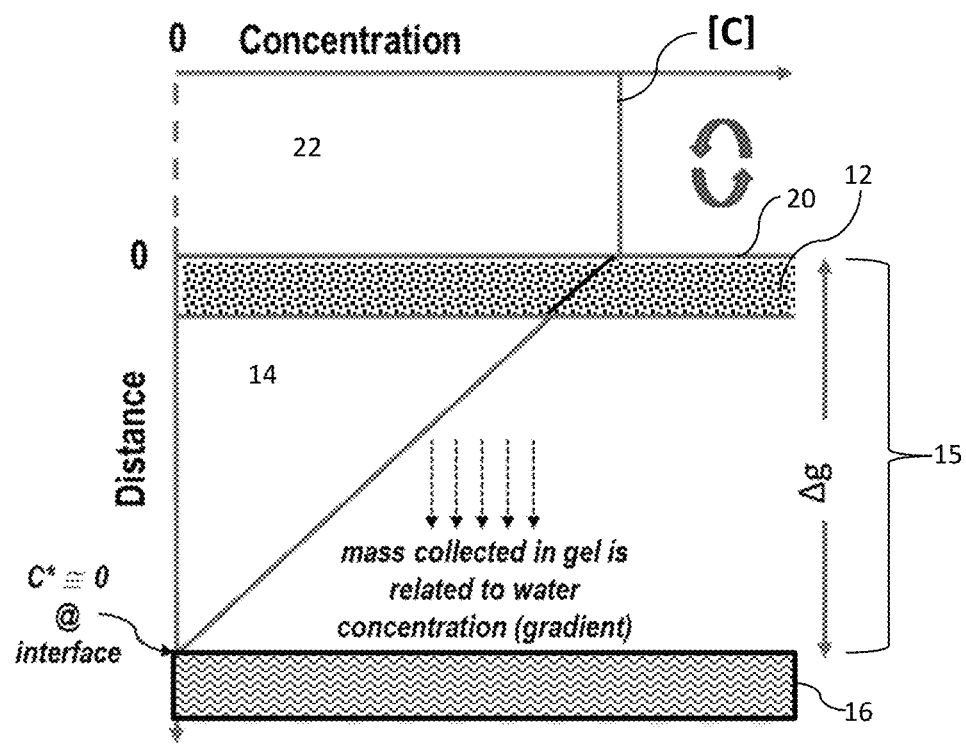
FIG. 2 depicts the concentration gradients across a DGT during typical operation with an aqueous solution sample.

As illustrated in FIG. 2, during use, upon exposing for a select amount of time (t) the upgradient end 20 of a DGT probe to a bulk fluid 22 that includes an analyte, a concentration gradient is established across the diffusive zone 15. This concentration gradient is determined by the concentration [C] of the analyte in the bulk fluid 22 combined with the understanding that the concentration of the sample carrier material (e.g., water, air, etc.) will be very low (e.g., $C^* \sim 0$) at the interface of the diffusive zone 15 and the capture layer 16.

By use of Fick's first law of diffusion, the mass (M) of the targeted material collected at the capture layer 16 can be related to the solution concentration C of the targeted material through the following equation:

$$C = \frac{M \Delta g}{DtA} \quad (1)$$

Where
$\Delta g$ is the thickness of the diffusion layer,
D is the diffusion coefficient ($cm^2/sec$) of the targeted material through the diffusion zone,
A is the surface area exposed to the solution ($cm^2$) (e.g., the cross-sectional surface area of the top 20), and
t is the time of exposure.

DGT technology is an economical and rapid passive sampling technique capable of monitoring target contaminants in fluids, and has proven to be an efficient in situ technique to measure total Hg in an aqueous sample. However, it has not been capable of passive separation of Hg species in a fluid sample. The presently disclosed devices and methods provide this capability.

Figure 3:
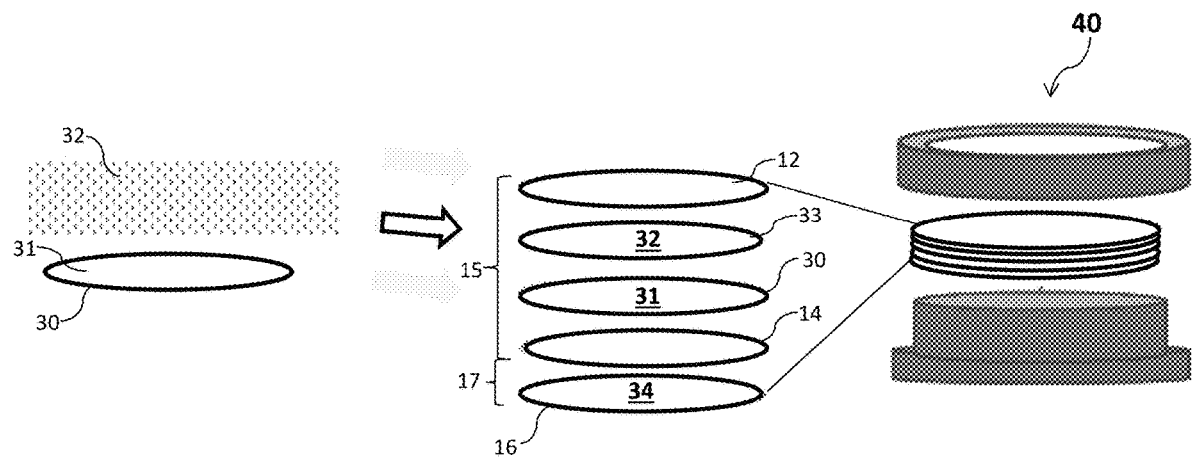
FIG. 3 schematically illustrates one embodiment of a passive sampling device as described herein.

FIG. 3 schematically illustrates one embodiment of a passive sampling device 40 as disclosed herein. To provide for speciation in Hg in passive sampling technologies, a sampling device 40 can incorporate certain aspects of DGT technology with the addition of reactive chemistry so as to selectively separate Hg species as they pass through a sampling device. Separation can be carried out by selective reaction and capture of targeted Hg species. More specifically, a device 40 can include a reactant 32 that can react with a first targeted Hg species of a fluid sample, but this reactant 32 does not react with other non-targeted Hg species that may be present in the fluid sample. The device can also include a sequesterant 31 that can selectively retain a second targeted Hg species, but does not retain other, non-targeted Hg species that may be present in the fluid sample.

The reactant 32 can generally be any material that can selectively react with the first targeted Hg species of a fluid sample. By way of example, in one embodiment the reactant 32 be a reductant that can react with inorganic Hg species of a fluid sample including labile Hg complexes (e.g., $HgCl_2^0$) and ionic Hg species (e.g., $Hg^{2+}$ and/or $Hg^{1+}$) to form elemental Hg. Hg reductants as are known in the art can be utilized including, without limitation, stannous salts (e.g., stannous chloride, Sn(II)Cl), elemental copper, elemental zinc, etc., as well as combinations of one or more Hg reductants.

The sequesterant 31 can selectively retain a targeted Hg species while allowing other Hg species to pass by and continue to diffuse toward the downgradient end of the device 40 without retention. The sequesterant 31 can retain the targeted species by any useful retention chemistry including covalent or noncovalent bond formation, e.g., charge/charge interaction, adsorption, absorption, etc.

In one embodiment, the sequesterant 31 can be configured to selectively retain a reaction product formed through reaction of the reactant 32 with the first targeted Hg species. For example in those embodiments in which the reactant 32 is a reductant that can reduce inorganic Hg species to form elemental Hg, the sequesterant can be an elemental metal that can selectively retain the second Hg species, i.e., the elemental Hg, through formation of an amalgam.

Almost all metals can form an amalgam with elemental Hg, with notable exceptions including iron, platinum, tungsten, and tantalum. As such, in one embodiment, the sequesterant 31 can include one or more amalgam-forming elemental metals. However, some metals are more efficient at amalgam formation than others. Accordingly, in some embodiments, it may be beneficial to incorporate such a metal. By way of example, in one embodiment a sequesterant 31 can include elemental gold, silver, copper, zinc, tin, or combinations thereof, optionally in conjunction with one or more additional amalgam-forming materials, so as to selectively retain elemental Hg formed via reaction of the reactant 32 with inorganic Hg of a fluid sample.

In one particular embodiment, the sequesterant 31 can be the same material as the reactant 32. For instance, copper and zinc can both function as a reductant for ionic and inorganic Hg species. In addition, copper and zinc can both amalgamate with elemental Hg. Accordingly, in one embodiment, incorporation of copper and/or zinc in a device 40 can provide both the reactant 32 and the sequesterant 31.

The location of the reactant 32 and the sequesterant 31 in the device is not particularly limited, and both can be independently located in either the diffusive zone 15 or the capture zone 17. However, in those embodiments in which the sequesterant 31 is configured to selectively retain a reaction product of the reactant 32, the sequesterant 31 will by necessity be located either downgradient or in the same general area (e.g., in the same layer) of the device as the reactant 32.

Figure 4:
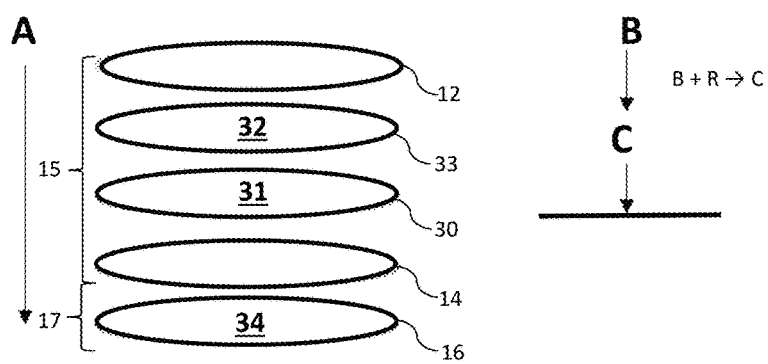
FIG. 4 schematically illustrates one exemplary use of the passive sampling device of FIG. 3.

In the embodiment illustrated in FIG. 3, the device 40 includes a diffusive zone 15 that includes, in addition to the filter layer 12 and the diffusion layer 14, a layer 30 and a layer 33. As shown, the layer 33 carries the reactant 32 and the layer 30 is downgradient to the layer 33 and carries the sequesterant 31. In this particular embodiment, and as schematically illustrated in FIG. 4, a sample applied to the upgradient end of the device 40 will first encounter a filter layer 12 where sediments or other solids can be separated from the remainder of the sample. Downgradient to the filter layer 12, the sample fluid can contact the layer 33, within which a first Hg species of the sample (species B in the right panel of FIG. 4) can react with the reactant 32 (species R in the right panel of FIG. 4) to form a second Hg species (species C in in the right panel of FIG. 4) according to the reaction B+R→C, as shown. Downgradient of the layer 33, the fluid (now carrying the reaction product C) can contact the layer 30, within which the sequesterant 31 can selectively retain a second Hg species, e.g., the reaction product C. Thus, species C will pass no further through the device 40 and will not pass through the diffusion layer 14 or into the capture zone 17 within which is a capture layer 16. However, the remainder of the sample fluid, and in particular any Hg species not selectively retained at the sequesterant 31 (illustrated as species A in the left panel of FIG. 4) can pass through the layer 30 and through the diffusion layer 14 and on into the capture zone 17 that carries the capture layer 16. In one embodiment, discussed further herein, the capture layer can be configured to non-selectively capture all Hg species. As such, any remaining Hg species (i.e., those not selectively retained by the sequesterant 31 in the layer 30, can be captured in the capture layer 16 by the agent 34.

As mentioned previously, however, the particular locations of the reactant 32 and the sequesterant 31 are not limited to the embodiment illustrated in FIG. 3, and the reactant 32 and sequesterant 31 can be located in any suitable layer or zone of a device. For instance, in the embodiment illustrated in FIG. 5, the reactant 32 and the sequesterant 31 are co-located in the same layer 30. In this embodiment, the reactant 32 and the sequesterant 31 are both located in a layer 30, that is between the filter layer 12 and the diffusion layer 14, and as such layer 30 is a component of the diffusive zone 15. As shown, a first Hg species B can react with the reactant R to form a second Hg species C according to the reaction B+R→C within the layer 30, and the reaction product C can also be selectively retained by the sequesterant 31 within the layer 30. As the reactant 32 and the sequesterant 31 are both located in the layer 30, both the reaction and the selective retention can take place in layer 30 and the second Hg species C will not pass into the diffusive layer 14. However, other Hg species A that are not selectively retained by the sequesterant 31, can pass through the diffusive layer 14 and be retained by the agent 34 at the capture layer 16 of the capture zone.

Figure 6:
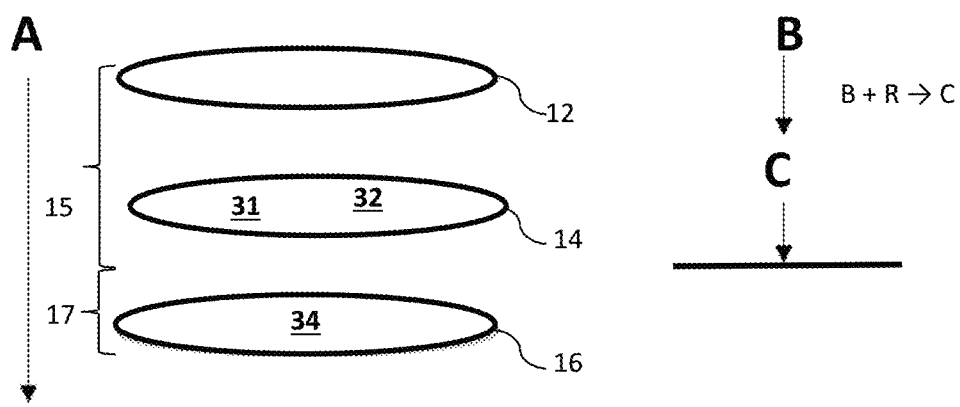
FIG. 6 schematically illustrates another embodiment of a passive sampling device as described herein.

FIG. 6 illustrates another embodiment of a device. In this embodiment, the diffusive zone 15 of the device includes a filter layer 12 and diffusion layer 14, similar to those know in prior art devices, but in this case the diffusive layer can incorporate both the reactant 32 and the sequesterant 31, without the addition of any other layers to the device. As such, the second Hg species that is formed upon reaction of the first Hg species with the reactant 32 according to the reaction B+R→C can be retained on/in the diffusion layer 14 by the sequesterant 31, while other Hg species A can pass on to be captured at the capture layer 16 via agent 34. Of course, in this embodiment, the reactant 32 can alternatively be in a separate layer that is upgradient to the diffusion layer, as discussed previously.

Figure 7:
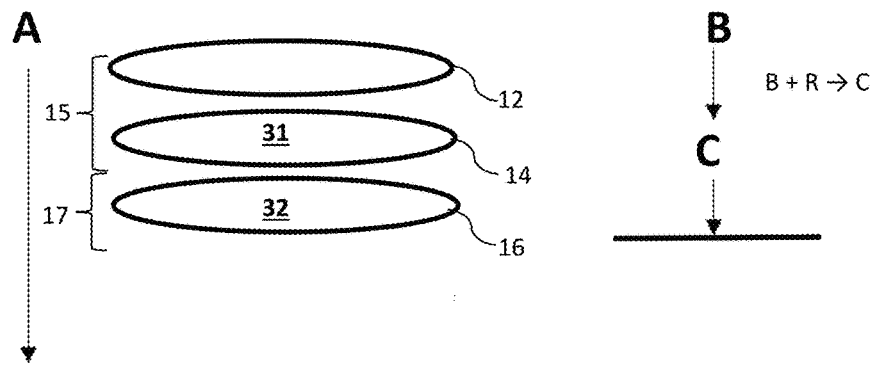
FIG. 7 schematically illustrates another embodiment of a passive sampling device as described herein.
Figure 8:
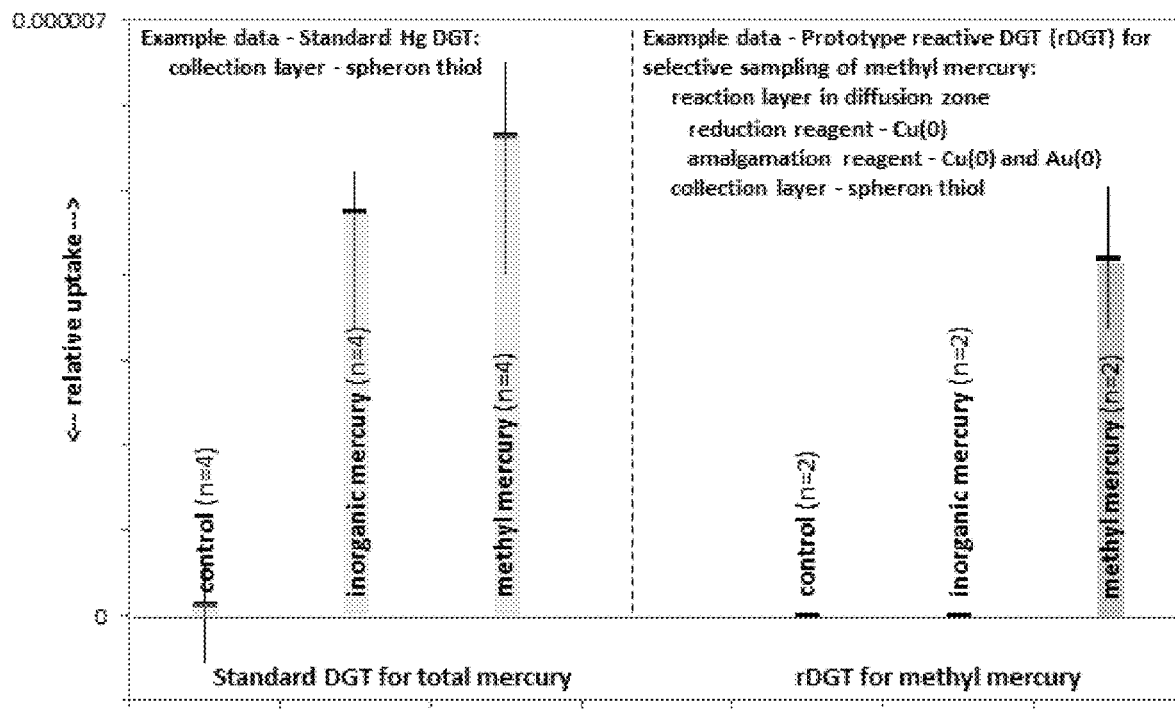
FIG. 8 graphically illustrates Hg speciation results by use of a device as described in the examples provided herein.

FIG. 7 illustrates yet another embodiment of a device as disclosed. In this embodiment, the device need not include the agent that non-selectively retains those Hg species not retained via the sequesterant 32. Thus, in this embodiment, only the predetermined targeted species are retained. As such, the sequesterant 32 can be present in the capture layer 16 of the capture zone 17. The reactant 31 can be upgradient of the sequesterant 32 or in the same layer as the sequesterant as described. In the embodiment illustrated in FIG. 7, the reactant 31 is upgradient of the sequesterant and located in the diffusion layer 14 of the diffusive zone 15. Of course, and as described above, the reactant 31 could alternatively be located in a different layer of the diffusive zone 15 or in a different layer of the capture zone. In this embodiment, any Hg species present in the fluid sample and not retained by the sequesterant can simply pass out of the downgradient end of the device.

Other arrangements of the reactant 31, sequesterant 32, and, when present agent 34, are well within the understanding of one of ordinary skill in the art.

Whatever the arrangement of the materials, a device 40 can include amounts of the sequesterant 31 and the reactant 32 so as to efficiently react with and retain the targeted species without interfering in flow of remaining Hg species through the device. For instance a supporting layer (e.g., a porous layer 30) that includes the reactant and/or the sequesterant within or on a matrix of the layer can generally include from about 0.05% to about 20% by weight of the active material(s) (i.e., the total amount of reactant and/or sequesterant) as compared to the weight of the layer material absent the active materials. This range can be larger or smaller, however for some embodiments.

Referring again to the embodiment schematically illustrated in FIG. 3, in this embodiment, the device 40 includes additional layers 30, 33 that are both a component of the diffusive zone and located upgradient of the of the diffusion layer 14, as shown, and that can carry the reactant 32 and the sequesterant 31. The layers 30, 33 can include a support structure or can be formed of the active material with no additional support structure. For instance, in the embodiment of FIG. 3, the reactant 32 can simply be applied to the surface of another layer 30 that does include a support structure, and can thereby form a layer 33 that is upgradient to the layer 30. For example an amount the reactant 32 (e.g., a stannous salt, copper-containing particulates, etc.) can be applied to the upgradient surface of the support structure of layer 30 to form an adjacent layer 33 upgradient of the layer 30.

Figure 5:
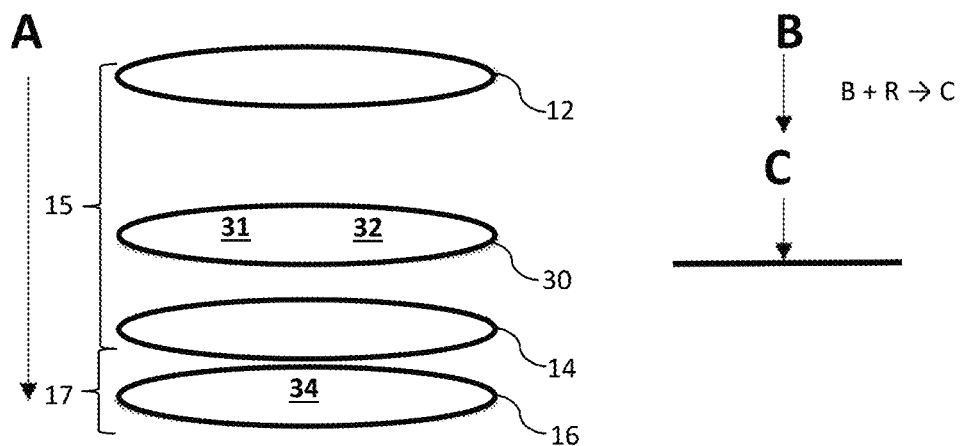
FIG. 5 schematically illustrates another embodiment of a passive sampling device as described herein.

When present, the support structure of a layer can generally include a porous matrix within which the reactant and/or the sequesterant can be loaded or impregnated. For example, and as illustrated in FIG. 3 and FIG. 5, a diffusive zone 15 can include a layer 30 in addition to the filter layer 12 and diffusion layer 14 as known in previously known DGT samplers, and the layer 30 can include a support structure that has been loaded with one or both of the reactant 32 and the sequesterant 31.

An active material (i.e., a reactant 32 or a sequesterant 31) can be incorporated in a device in conjunction with a supporting substrate such as a supporting particle, fiber, or membrane to which the active material is adhered. In general, a supporting substrate can have a high surface area, e.g., in a range of about 20 $m^2/g$ to about 800 $m^2/g$.

An active material can be an integral component of a formation material of a supporting substrate. For instance a polymer used to form the supporting substrate (e.g., a particle or a fiber) can include a functionality that selectively binds to or selectively reacts with an Hg species. In another embodiment a supporting substrate can be processed to carry the active material. For instance, a high surface area particulate substrate such as silica, alumina, zirconia, etc. can be coated with one or both of a reactant 32 and a sequesterant 31.

In one non-limiting example, a particulate substrate can be coated with a solution that provides the sequesterant 31. For instance, a solution of a metal salt (e.g., a methanol based solution including a combination HCl/methanol/hexane solvent and a gold chloride in an amount up to saturation of the solution) can be applied to a particulate substrate (by e.g., simply soaking the particulate in the solution). Following, the solvent can be removed (by e.g., air drying or applied heat) and the metal salt reduced to provide an elemental metal sequesterant that is carried by a particulate substrate.

In another embodiment, a high surface area, uncoated, supporting substrate (such as silica) can be first loaded into the support structure of a layer (e.g., layer 30), and the layer can subsequently be treated with a solution so as to apply the sequesterant, reactant, or a precursor thereof; such as a solution of gold chloride to the supporting substrate. The solution can coat the surface of the supporting substrate as well as pores of the support structure of the layer. Following, the layer can be further treated to provide the selective material. For example, a metal salt can be reduced to provide elemental gold on/in the layer 30.

A reactant 32 can be incorporated in a single layer of a device in conjunction with the sequesterant 31 or separately, as desired. For instance, in one embodiment, a first supporting substrate can carry a sequesterant 31 and a second supporting substrate (that can be of the same or different formation materials as the first supporting substrate) can carry a reactant 32. Alternatively, both the sequesterant 31 and the reactant 32 can be carried by a single supporting substrate. For instance, a particulate substrate can be contacted with a solution of the reactant 32 under conditions to encourage retention of the reactant 32 on the particles and following, the particulate substrate can be contacted with a second solution (e.g., a metal salt solution) under conditions to encourage retention of the sequesterant on the particles.

A supporting substrate can be incorporated into the support structure of a layer by any means. By way of example, the supporting substrate can be added directly to the layer formation materials during or following formation, and the support structure of the layer can then be placed under pressure, e.g., calendared, to enmesh the supporting substrate in the support structure of the layer. In another embodiment, a supporting substrate can be incorporated into a primary binder system that is applied to components that form the layer (e.g., the fibers). Curing of this binder can adhesively attach the substrate to the support structure of the layer. In a third embodiment, a secondary binder system can be introduced into the layer following addition of a supporting substrate to the layer. The secondary binder can then be cured (independent of any primary binder of the layer itself) to adhesively incorporate the supporting substrate into the support structure of the layer. In yet another embodiment, a binder structure (e.g., a binder fiber) can be been introduced into a layer during formation, for instance during an air laying or carding process. Following, the layer can be heated above the softening temperature of the binder structure, and this can adhesively capture the supporting substrate that has been introduced into the support structure of the layer.

The various layers of a device 40 can be formed of any suitable matrix. For instance a layer 30 that is incorporated upgradient of a typical diffusion layer 14 and downgradient of a typical filter layer 12 can be of any suitable material and construction so as to allow diffusion therethrough (e.g., including pores in a range of from about 0.3 µm to about 5 µm). For instance, a layer 30 can be of the same or similar construction as a typical filter layer 12 as is known in previously known DGT sampling devices.

The materials of formation for a layer 30 are not particularly limited and can include, without limitation, organic or inorganic polymers, glass, quarts, ceramic or any combination thereof. Organic polymers as may be utilized in forming a layer 30 can include, without limitation, cellulose, polyamides (e.g., nylons), polyolefins, polyesters, polyurethanes, polyvinylhalides, or a combination thereof. In one embodiment, a porous membrane can include polytetraflouroethylene (PTFE) as a material of formation.

A layer 30 can be of a fibrous construction. Suitable fibers can include, and without limitation to, polymeric fibers, glass fibers, quartz fibers, ceramic fibers, or any combination thereof. A fibrous web for us in forming a layer 30 can include fibers of any suitable diameter. For instance, a nonwoven fibrous web can include a plurality of microfibers, for instance of thermoplastic, melt-blown polymeric materials. As utilized herein, the term microfiber generally refers to fibers having an average fiber diameter of about 50 µm or less, for instance from about 2 µm to about 25 µm in some embodiments. A fibrous web is not limited to incorporation of microfibers, however, and a porous layer 30 can incorporate large-diameter fibers, for instance large diameter melt-extruded fibers that have been mechanically-calendared, air-laid, or spunbonded in formation of a porous layer 30. As utilized herein, the term "large-diameter fiber" generally refers to fibers having an average fiber diameter of about 50 µm to about 500 µm. By way of example, a non-woven web made from large-diameter staple fibers as can be formed on carding or air-laid machines as is well known in the art can be utilized in forming a porous layer. A layer 30 is not limited to utilization of fibrous membranes, however, and non-fibrous porous materials may alternatively be utilized.

In general, no matter what the materials of formation are, a layer 30 can be relatively thin, e.g., about 1 mm or less in thickness between the first side and the opposite second side. For instance a layer 30 can be from about 100 μm to about 500 μm in thickness, in some embodiments.

In conjunction with a reactant 32 and a sequesterant 31, a device can include other components as are known for use in previously known DGT passive samplers. For example, a device can include a filter layer 12. The filter layer 12 can have a construction and be formed of materials as described above with regard to a layer 30. For instance, the filter layer 12 can include pores in a range of about 0.3 μm to about 5 μm, can be fibrous or non-fibrous in nature, with exemplary formation materials including, but not limited to, polymers, glass, quartz, ceramic, or any combination thereof.

A filter layer 12 can be particularly beneficial when utilizing a device in an in situ environmental application, for instance for removal of sediment from a liquid sample prior to the sample diffusion through the remainder of the device. As such, the filter layer 12 can describe a porosity that can vary depending upon the particular characteristics of the application and the sample materials to be analyzed. For instance, when considering applications in which the fluid sample is expected to be a gaseous or vaporous sample, the porosity of the filter layer 12, can be smaller than in those applications in which the fluid sample is expected to be a liquid. Such modifications are well within the skill level of one of ordinary skill in the art.

A sampling device can also include a diffusion layer 14 as is known for Hg DGT sampling systems. The diffusion layer can include a hydrogel that can allow for diffusion of Hg species in a time and concentration dependent manner, as discussed above. For instance, as Hg has a high binding capacity with amide groups, it may be preferred in some embodiments to avoid use of a polyacrylamide gel (as is common in other DGT applications) in forming the diffusion layer 14. In other embodiments, a diffusion layer 14 can include a polyacrylamide, e.g., a polyacrylamide gel. In one embodiment, the diffusion layer 14 can include an agarose hydrogel (e.g., from about 0.5 w/v % to about 2 w/v % agarose).

A diffusion layer 14 can generally have a thickness as is known in the art for Hg sampling DGT devices. For instance, the diffusion layer 14 can generally have a thickness of from about 0.5 mm to about 2 mm, or from about 0.5 mm to about 1.5 mm in some embodiments.

The kinetics of Hg transport across the diffusive zone 15 is controlled by the diffusion coefficient of the Hg species, which is defined by the characteristics of the Hg species being transported (e.g., size, ionic characteristics, etc.), compared to the characteristics of the diffusive zone 15 and the different layers of the diffusive zone 15, e.g., pore size, etc. In general a diffusive layer 14 can include a hydrogel matrix that can exhibit a pore size of about 10 nm or less, for instance from about 2 nm to about 5 nm. As is known, the thickness of the diffusion layer 14 can be predetermined based upon the Hg species to be collected at the capture layer 16 and the desired mass transport rate across the gel. As transport across the gel is restricted to diffusion, selection of the gel thickness can be utilized to control the overall rate of mass transport across the diffusion layer 14, irrespective of the hydrodynamics of the bulk sample solution being tested by the device.

Downgradient of the diffusive zone 15, the device can include a capture zone 17 that can include a capture layer 16. The capture layer 16 can generally include a hydrogel and a capture material. As discussed above, in one embodiment the capture material of the capture layer 16 can include a binding agent 34 that can retain Hg species that have not been selectively captured previously by the sequesterant 31. As such, the binding agent 34 of the capture layer 16 need not selectively bind Hg species, but can incorporate generic Hg complexing agents capable of retaining multiple Hg species thereon. For instance, the capture layer can be similar to capture layers utilized in previously known passive sampling devices for non-specific Hg binding. By way of example, agents capable of forming a complex with a Hg-containing species such as, and without limitation to, organic thiols and/or dithiocarbamates in combination with $Au^{+3}$ or other complexing agents such as acidic mixtures containing dithiol species can be utilized.

In one embodiment, the capture layer 16 can incorporate as binding agent 34 an ion exchange resin capable of retaining multiple Hg species thereon. For instance, a capture layer 16 can include a thiol-functionalized resin gel, e.g., a thiol-functionalized resin incorporated into a polyacrylamide or other suitable hydrogel. In one particular embodiment, a capture layer 16 can include a 3 mercaptopropyl functionalized silica gel immobilized in a polyacrylamide gel.

As described and illustrated in FIG. 6, in another embodiment, a capture layer 16 can be fabricated to include the sequesterant 31. In this embodiment, only Hg species that are selectively retained by the sequesterant 31 can be captured at the capture layer 16. Other non-targeted Hg species would not be retained at the sequesterant 31 located in the capture layer and would not be collected.

A capture layer 16 can generally have a thickness on the order of that of the filter layer 12 and, when present, a layer 30. For instance, a capture layer 16 can be relatively thin, e.g., about 1 mm or less in thickness, for instance from about 100 μm to about 500 μm in thickness, in some embodiments.

Following placement in contact with a sample for a predetermined amount of time, the capture zone 17 of a device can be analyzed to determine the presence or quantity of the Hg species retained by either the sequesterant 31 or the binding agent 34, depending upon the specific structure of a device. More specifically, following completion of a sampling protocol, the capture layer 16 can be examined for either direct or indirect determination of the presence or quantity of the Hg species retained thereon. Indirect determination methods can include, for example and without limitation to, elution of Hg species off of the capture layer followed by examination of the eluent. Direct determination methods can include, for example and without limitation to, mass analysis of the layer.

In one embodiment, a species determination protocol can be combined with a generic Hg sampling protocol. For example, a first protocol can be carried out by use of a device as described herein, which can provide for quick and economical determination of a particular Hg species present in a sample (e.g., the organic Hg species captured at the capture layer 16). A second protocol can then be run with a sample obtained from the same source using a typical Hg DGT passive sampler as previously known in the art (or any other sampling protocol) that can provide for determination of the total Hg content of a sample. Comparison of the two results can provide additional information about the sample source, such as the presence or quantity of the Hg species that was selectively retained at the porous layer.

Disclosed methods and devices can be utilized to provide improved information of Hg presence and activity in sample sources. For instance, as methyl Hg is selectively taken up by aquatic invertebrate species, devices that selectively retain methyl Hg at a layer can serve as a surrogate for aquatic organisms.

Devices can be conveniently utilized in a wide variety of locations and applications. In particular, devices can be utilized in both liquid (e.g., aqueous) applications as well as for Hg speciation of gaseous or vaporous samples. Beneficially, as the devices are passive sampling devices, they can be utilized in a wide variety of locations, including remote locations. For example, devices can be utilized to sample water sources (e.g., fresh or salt water; lakes, rivers, ponds, swamps, etc.; underground (e.g., wells) or above ground, etc.) as well as air sources (e.g., industrial off-gases, high or mid-level atmospheric samples, etc.), just to name a few.

The present disclosure may be better understood with reference to the Example set forth below.

Example

DGT's were supplied by DGT Research Ltd, Lancaster A2 0QJ, UK. A DGT as supplied containing a spheron-thiol resin intended for total Hg capture was utilized as a comparison device.

Inventive devices were formed to include an additional filter beneath the upper-most filter of the retail devices. This additional filter was conditioned with colloidal gold (3 nm) by soaking in about 20 ppm of gold solution followed by drying by placing it in an oven at 95° C. for about 3 hours.

To form a first inventive device, stannous chloride powder was prepared and finely grounded using a mortar and pestle. About 0.1 g of the powder was placed between the upper-most filter and the additional, colloidal gold-containing filter to encourage amalgamation between elemental Hg formed by reaction with the reductant and colloidal gold before the sample solution met the diffusion layer.

To form a second inventive device, 0.16 g of copper metal powder was placed between the uppermost filter and the additional, colloidal gold-containing filter, instead of the stannous chloride of the first inventive device.

Artificial stream water was made in 10 L batches using Nalgene containers by mixing 0.01 g potassium chloride, 0.307 g magnesium sulfate heptahydrate, 0.150 g calcium sulfate dehydrate, and 0.240 g sodium bicarbonate, and NANOpure® Diamond deionized water with a conductivity of 18.2 megaohms-cm.

Analysis of the capture resins of the devices was carried out by use of a Lumex® RA915+ Zeeman Effect Spectrometer, which uses a pyrolytic technique that converts all Hg to elemental Hg to determine Hg concentration within a sample.

Standard calibration tests were run during which the capture resins of the comparison and inventive devices were spiked with a known amount of Hg standard and placed in the Lumex® glass ladles for analysis. This same procedure was also done with standard water samples spiked with the same amount. The standards were tested in the Lumex® to create calibration curves for MeHg and inorganic Hg (InHg).

Testing solutions were formed. Artificial stream water solution was spiked with Hg standards to create a solution containing 1200 mg/L concentration of inorganic Hg ($Hg^{2+}$ and $HgCL_2$) and a solution containing 1200 mg/L MeHg. A magnetic stir bar was placed in each beaker and then placed on a stir plate set on a low speed to allow for gentle mixing. The solutions in each beaker equilibrated before placing the comparison and inventive devices into the beakers to compensate for Hg stability.

For sample testing, devices were taken out of the cold room (39° F.) where they had been stored in polyethylene bags. Removal from the storage bags was carried out so as to avoid contamination of the top filter membrane. Monofilament line was attached to holes in the base of the device housings so that they devices could be fully immersed in the sample solutions. The devices were immersed for 48 hours.

Water samples were removed from each sample solution. The organic Hg in these water samples was converted to an elemental state through addition of 1 mL of bromine monochloride (BrCl). The reagent was prepared as described in EPA Method 1631. After the water samples were preserved with bromine monochloride, they were analyzed using EPA Method 7470. The deployment/harvest concentrations were averaged and the resulting value was used in the DGT equation (2) provided below for interpreting the various tests.

At the end of the immersion time periods, the devices were retrieved without touching the uppermost filter membrane. The devices were then rinsed with deionized water and shaken to remove any surface water still present. The devices that were not analyzed immediately were placed in individual polyethylene bags with minimum air space. Each bag was labeled and placed in cold storage.

Capture gel samples were analyzed using Lumes® 915+ zeeman effect spectrometer equipped with a Lumex® yyy solids (desorption/pyrolysis) attachment. The quartz ladles were lined with aluminum foil and baked out. Each sample/standard was placed on the aluminum foil and covered with approximately 1.5 g of a mixed powder of sodium carbonate ($NaCO_3$) and copper oxide (CuO)—50% each by mass. The mixed powder was then placed in the oven at 95° C. for 24 hours before use. Use of the powder reduced smoke formation and aided in converting all of the Hg in the capture gel samples into elemental Hg for accurate detection. The loaded ladles were placed in the instrument and heated to 700° C. Hg was released into the spectrometer for quantitation.

For analysis, the cap of each device was twisted open and the hydrogel resin capture layer was removed. The resin was placed in a clean glass ladle lined with aluminum foil and covered with the $NaCO_3$ and CuO mix.

The performance of each device was assessed by estimating an apparent diffusion coefficient, $D^*$:

$$D^* = \frac{M \Delta g}{CtA} \quad (2)$$

In which:
$\Delta g$ is the diffusive zone thickness which is the sum of the thicknesses of the diffusion gel, the filter membrane, and the supplemental reactants thickness,
M is the measured mass of Hg collected onto the gel,
$D^*$ is the calculated apparent diffusion coefficient of Hg in the gel,
t is the deployment time, and
A is the exposure area.
If a device performed well, $D^*$ would be similar to the theoretical value and within the bounds of the values measured in the literature for Hg devices. Low values of $D^*$ indicated that the devices was not effectively collecting the analyte and indicated that the targeted Hg was not being effectively and completely taken up by the collection gel, and/or Hg was being trapped in the diffusion zone (e.g., by reaction or sorption).

FIG. 5 presents results data comparing the comparison device with the second inventive device that included copper metal powder as the reactant and elemental gold as an amalgamation agent. As shown, the differential uptake between the species in the capture layer was significant. In comparison between the stannous-based inventive device and the cupric-based inventive device, there was an improvement in the differential uptake between MeHg and InHg at the capture gel with the change in reductant from $SnCl_2$ to Cu(0). It was also observed that in utilizing solid Cu(0) as a reductant, no precipitation of reagent was observed in the external immersion solution.

While certain embodiments of the disclosed subject matter have been described using specific terms, such description is for illustrative purposes only, and it is to be understood that changes and variations may be made without departing from the spirit or scope of the subject matter.

What is claimed is:

1. A passive mercury sampling device comprising:
   an upgradient end and a downgradient end;
   a diffusive zone;
   a capture zone downgradient of the diffusive zone;
   a reactant located upgradient of the capture zone, the reactant being configured to react with a first mercury species;
   a first sequesterant located either downgradient of the reactant or in a layer with the reactant, the first sequesterant being configured to selectively retain a second mercury species, wherein a reaction between the first mercury species and the reactant forms the second mercury species; and
   a mercury capture agent located within the capture zone, the mercury capture agent being either a non-specific mercury capture agent configured to retain multiple different mercury species or a second sequesterant configured to selectively retain a third mercury species that differs from the first mercury species and the second mercury species.

2. The passive mercury sampling device of claim 1, wherein the reactant and the first sequesterant are both located in or upgradient of the diffusive zone.

3. The passive mercury sampling device of claim 1, wherein the reactant is upgradient of the first sequesterant.

4. The passive mercury sampling device of claim 3, wherein the reactant is located upgradient of the diffusive zone and the first sequesterant is located in the diffusive zone.

5. The passive mercury sampling device of claim 1, wherein the diffusive zone and/or the capture zone each independently comprise multiple layers.

6. The passive mercury sampling device of clam 1, wherein the diffusive zone and/or the capture zone comprises a hydrogel.

7. The passive mercury sampling device of claim 1, wherein the first sequesterant is configured to retain elemental mercury.

8. The passive mercury sampling device of claim 7, wherein the first sequesterant comprises an elemental metal.

9. The passive mercury sampling device of claim 8, wherein the elemental metal comprises gold, silver, copper, zinc, tin or any combination thereof.

10. The passive mercury sampling device of claim 7, wherein the mercury capture agent is configured to retain methyl mercury.

11. The passive mercury sampling device of claim 1, wherein the first sequesterant is carried by a supporting substrate.

12. The passive mercury sampling device of claim 11, wherein the supporting substrate is a particulate substrate, a fibrous substrate, or a membrane substrate.

13. The passive mercury sampling device of claim 1, wherein the reactant is a reductant.

14. The passive mercury sampling device of claim 1, wherein the first sequesterant and the reactant are the same material.

15. A method for selectively sampling a mercury species, comprising:
    contacting a fluid sample with the upgradient end of the passive sampling device of claim 1, the fluid sample comprising the first mercury species, wherein upon the contact, the first mercury species reacts with the reactant to form the second mercury species, the second mercury species thereafter being selectively retained by the first sequesterant;
    analyzing the capture zone to determine a presence or quantity of all mercury species in the capture zone; and
    analyzing the first sequesterant to determine a presence or quantity of the second mercury species retained thereby; wherein
    the method determines a presence and/or concentration of each of at least two different mercury species in the fluid sample.

16. The method of claim 15, wherein the first sequesterant is located in the diffusive zone such that the second mercury species is retained in the diffusive zone.

17. The method of claim 15, wherein the fluid sample is an aqueous liquid sample.

18. The method of claim 15, wherein the first mercury species comprises an inorganic mercury species or an ionic mercury species.

19. A method for selectively sampling a mercury species, comprising:
    contacting a first fluid sample obtained from a sample source with an upgradient end of passive sampling device the first fluid sample comrising a first mercury species, the passive sampling device comprising a diffusive zone and a capture zone that is downgradient of the diffusive zone, the passive sampling device further comprising a reactant configured to react with the first mercury species to form a second mercury species and comprising a sequesterant configured to selectively retain the second mercury species, the reactant and the sequesterant each being independently located in either the diffusive zone or the capture zone, the sequesterant being downngradient of or in a layer with the reactant; wherein upon the contact, the first mercury species reacts with the reactant to form the second mercury species, the second mercury species thereafter being selectively retained by the sequesterant;
    determining a quantity of the second mercury species retained by the sequesterant;
    analyzing a second fluid sample obtained from the sample source to determine total mercury content of the second fluid sample; and
    comparing the total mercury content of the second fluid sample with the quantity of the second mercury species retained by the sequesterant.

20. The method of claim 19, where the comparison comprises subtracting the quantity of the second mercury species from the total mercury content of the second fluid sample and assigning any remaining mercury content to one or more other mercury species of the sample source.

\* \* \* \* \*